United States Patent
Ozawa et al.

(10) Patent No.: US 7,860,217 B2
(45) Date of Patent: Dec. 28, 2010

(54) X-RAY DIFFRACTION MEASURING APPARATUS HAVING DEBYE-SCHERRER OPTICAL SYSTEM THEREIN, AND AN X-RAY DIFFRACTION MEASURING METHOD FOR THE SAME

(75) Inventors: Tetsuya Ozawa, Hino (JP); Ryuji Matsuo, Hino (JP); Go Fujinawa, Hamura (JP); Akira Echizenya, Fussa (JP)

(73) Assignee: Rigaku Corporation, Tokyo (JP)

( * ) Notice: Subject to any disclaimer, the term of this patent is extended or adjusted under 35 U.S.C. 154(b) by 0 days.

(21) Appl. No.: 12/238,471

(22) Filed: Sep. 26, 2008

(65) Prior Publication Data
US 2009/0086910 A1    Apr. 2, 2009

(30) Foreign Application Priority Data
Sep. 28, 2007    (JP)    ............................. 2007-253146

(51) Int. Cl.
*G01N 23/207*    (2006.01)
(52) U.S. Cl. .......................................... 378/75; 378/71
(58) Field of Classification Search .............. 378/70–90
See application file for complete search history.

(56) References Cited

U.S. PATENT DOCUMENTS

| | | | |
|---|---|---|---|
| 4,364,122 A | 12/1982 | Wolfel et al. | |
| 4,375,695 A | 3/1983 | Harding et al. | |
| 6,041,099 A | 3/2000 | Gutman et al. | |
| 6,226,349 B1 | 5/2001 | Schuster et al. | |
| 6,373,544 B1 | 4/2002 | Hirabayashi | |
| 2002/0003859 A1 | 1/2002 | Kogan | |
| 2002/0136352 A1 | 9/2002 | Protopopov | |
| 2004/0156471 A1 | 8/2004 | Sakata | |
| 2004/0208283 A1 | 10/2004 | Helming et al. | |

FOREIGN PATENT DOCUMENTS

| | | | |
|---|---|---|---|
| DE | 2933047 | | 2/1981 |
| DE | 2944147 | | 5/1981 |
| DE | 19833524 | | 2/2000 |
| DE | 10125454 | | 12/2001 |
| DE | 10317679 | | 11/2004 |
| EP | 1 233 265 | | 8/2002 |
| EP | 1 462 795 | | 9/2004 |
| JP | 04-161843 | | 6/1992 |
| JP | 08-062158 | | 3/1996 |
| JP | 2003-083915 | | 3/2003 |
| JP | 2003-149348 | * | 5/2003 |
| JP | 3721305 | | 9/2005 |
| WO | WO 86/03005 | | 5/1986 |

* cited by examiner

*Primary Examiner*—Jurie Yun
(74) *Attorney, Agent, or Firm*—Antonelli, Terry, Stout & Kraus, LLP.

(57) ABSTRACT

An X-ray diffraction measuring apparatus equipped with Debye-Scherrer optical system therein, comprises a generator for generating a characteristic X-ray to be irradiated upon a sample to be measured; an X-ray detector being disposed to surround that sample around; and a focusing arrangement, being disposed between the sample and the X-ray detector, for collecting an X-ray scattering from the sample covering over a predetermined angle, in a peripheral direction, around the sample, and for focusing and irradiating it upon the X-ray detector.

14 Claims, 6 Drawing Sheets

X-RAY DIFFRACTION MEASURING APPARATUS HAVING DEBYE-SCHERRER OPTICAL SYSTEM THEREIN, AND AN X-RAY DIFFRACTION MEASURING METHOD FOR THE SAME

BACKGROUND OF THE INVENTION

The present invention relates to an X-ray diffraction measuring apparatus for analyzing powder-like crystals or the like, with using an X-ray, and in particular, it relates to an X-ray diffraction measuring apparatus building up a Debye-Scherrer optical system therein, and also an X-ray diffraction measuring method for the same.

In general, various kinds of X-ray diffraction measuring apparatuses are already known, comprising the Debye-Scherrer optical system therein, for analyzing a sample of powder-like crystals, through measuring the diffraction rings (i.e., Debye rings), which can be obtained from that sample, in an angular direction around that, while irradiating a monochromatic X-ray thereupon.

By the way, with such X-ray diffraction measuring apparatus, comprising the Debye-Scherrer optical system therein, due to excessive scattering X-rays, such as, stray radiations, inelastic scattering, fluorescence X-rays, etc., for example, within the apparatus, which are detected by an X-ray detector, but other than the X-ray diffracted from the sample, to be detected inherently, a background noise component becomes large, and therefore a background comes to be high while a P/B ratio (Peak/Background ratio) is low. For that reason, within such the measuring apparatus, as is well-known by the following Patent Document 1 and Patent Document 2, it is common to apply an analyzer made from slits, which are partitioned in a fan-like shape or a radial manner, or a rocking or oscillation-type analyzer, which oscillates parallel slit-analyzers into an angular direction around a center of the sample.

[Patent Document 1] Japanese Patent Laying-Open No. Hei 8-62158 (1996); and

[Patent Document 2] Japanese Patent Laying-Open No. 2003-149348 (2003).

BRIEF SUMMARY OF THE INVENTION

However, with such the method of the conventional arts mentioned above, although the details thereof will be mentioned later, the analyzer mentioned above, being provided for reducing the background, brings about an eclipse (e.g., shielding) of the scattering rays (e.g., diffraction X-rays), and thereby this results into a lowering of measuring strength or intensity. Also, there are other problems: i.e., an increase of angular error due to shift or deviation of the position for mounting the sample thereon, and further a remarkable lowering of resolution power due to a size of the sample, etc.

Then, according to the present invention, accomplished by taking the problems of the conventional arts mentioned above into the consideration thereof, for dissolving the problems within the conventional arts mentioned above, in particular, within the X-ray diffraction measuring apparatus comprising the Debye-Scherrer optical system therein, i.e., an object thereof is to provide an X-ray diffraction measuring apparatus, having the Debye-Scherrer optical system therein, for dissolving the lowering of measuring strength or intensity due to the eclipse (e.g., the shielding) in the conventional analyzer, and thereby without the lowering of measuring strength or intensity, and further, without an increase of the angular error due to shift or deviation of the position for mounting the sample thereon nor a lowering of the resolution power due to a size of the sample, and also an X-ray diffraction measuring method for the same.

For accomplishing the object mentioned above, according to the present invention, there is provided an X-ray diffraction measuring apparatus equipped with Debye-Scherrer optical system therein, comprising: a means for generating a characteristic X-ray to be irradiated upon a sample to be measured; an X-ray detector means being disposed to surround said sample around; and a focusing means, being disposed between said sample and said X-ray detector means, for collecting an X-ray scattering from said sample covering over a predetermined angle, in a peripheral direction, around said sample, and thereby irradiating it upon said X-ray detector means.

Also, according to the present invention, in the X-ray diffraction measuring apparatus equipped with Debye-Scherrer optical system therein, as described in the above, it is preferable that said focusing means are attached in a plural number thereof, on a front surface of said X-ray detector means, or that said focusing means is attached to be movable, on a front surface of said X-ray detector means, or that said focusing means is built up with a mirror, which is made of artificial multi-layers having a parabolic surface. Further, it is preferable that said X-ray detector means is built up with a two-dimensional detector, such as, an X-ray sensitive film, an imaging plate, a CCD two-dimensional detector, etc., or a one-dimensional detector, such as, a PSD (Position Sensitive Detector), etc.

Further, according to the present invention, also for accomplishing the object mentioned above, there is provided an X-ray diffraction measuring method for Debye-Scherrer optical system, comprising the following steps of: irradiating a characteristic X-ray generated; collecting a scattering X-ray obtained through irradiation of said X-ray, covering over a predetermined angle around said sample; and obtaining a Debye ring by irradiating the scattering X-ray at a predetermined position on an X-ray detector means, being disposed in a peripheral direction, surrounding around said sample.

And, according to the present invention, the X-ray diffraction measuring method for Debye-Scherrer optical system, as claimed in the above, it is preferable that the scattering X-ray is collected by a mirror made of artificial multi-layers, covering over a predetermined angle around said sample, and is irradiated at a predetermined position on the X-ray detector, which is disposed to surround said sample around.

As is apparent from the above, according to the present invention, it is possible to achieve an extremely superior effect, i.e., providing an X-ray diffraction measuring apparatus comprising the Debye-Scherrer optical system therein and an X-ray diffraction measuring method for the same, for dissolving the reduction of scattering ray (i.e., the diffraction X-ray) due to the eclipse (e.g., shielding) thereof, thereby dissolving the lowering of measuring strength or intensity or deterioration of resolution power, and further without lowering of the resolution power thereof depending on size of the sample.

BRIEF DESCRIPTION OF THE SEVERAL VIEWS OF THE DRAWING

Those and other objects, features and advantages of the present invention will become more readily apparent from the following detailed description when taken in conjunction with the accompanying drawings wherein.

DETAILED DESCRIPTION OF THE PREFERRED EMBODIMENTS

Hereinafter, embodiments according to the present invention will be fully explained by referring to the attached drawings.

Figure 1A:
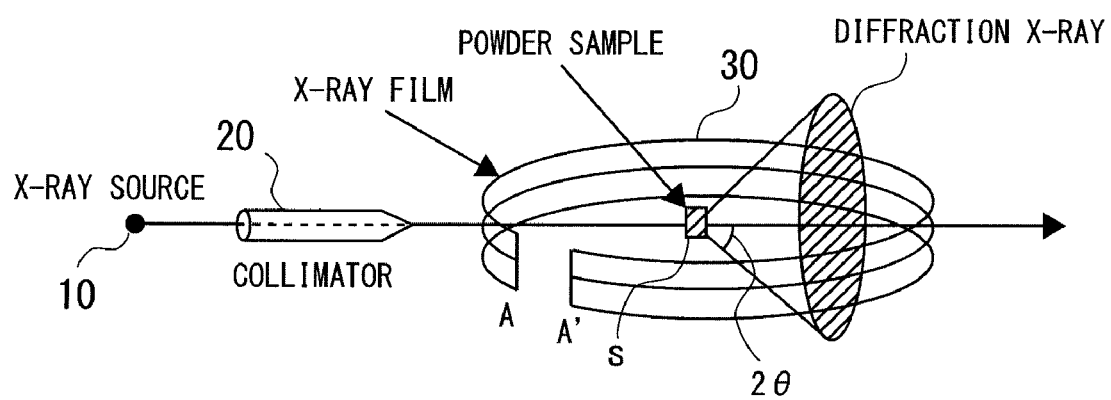
FIGS. 1A and 1B are views for showing an X-ray diffraction measuring apparatus having the Debye-Scherrer optical system therein, and for showing a stripe pattern (i.e., the Debye rings), which is obtained therefrom.
Figure 1B:
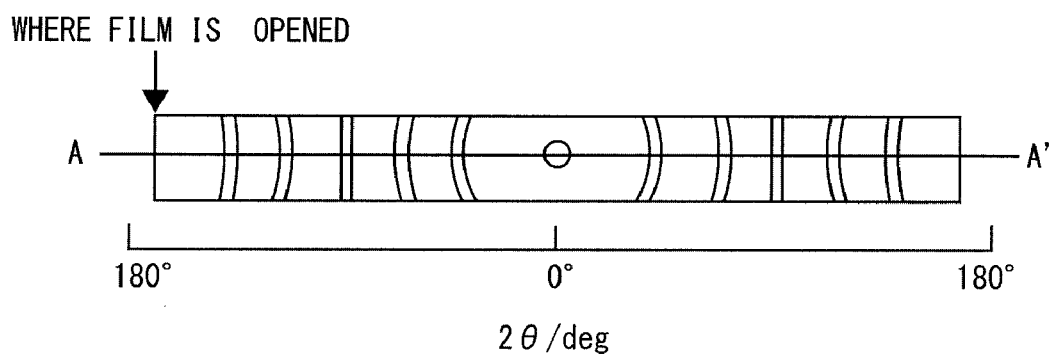

First of all, FIG. 1A attached herewith shows an outlook configuration of an X-ray diffraction measuring apparatus having the Debye-Scherrer optical system therein, wherein a monochromatic characteristic X-ray, which is emitted from an X-ray source 10 made of an X-ray tube, for example, is irradiated upon a sample S of polycrystalline substance, after being collimated into a parallel beam of a predetermined diameter through a collimator 20. As a result thereof, this irradiated X-ray scatters over a predetermined angle 2θ around that sample S, as an X-ray diffracted by that sample S of polycrystalline substance, and thereby being irradiated upon an X-ray detection means 30, being constructed with an X-ray film, which is cylindrically disposed on the periphery thereof, around that sample S, etc. As a result thereof, as is shown in FIG. 1B attached herewith, upon the X-ray film 30 can be obtain a stripe-like pattern (i.e., the Debye rings), at predetermined positions (or angles), on both sides thereof, around a center of irradiation direction of X-ray (2θ=0°).

Now then, with the analyzer made from the slits, which are partitioned in a fan-shaped or a radial manner, according to the conventional arts mentioned above, as shown in FIGS. 7A and 7B and 8A and 8B, an eclipse (or shielding) of the scattering beam (i.e., diffracted X-ray) by the analyzer and also an angular error at the position where the sample is mounted are large, and further a lowering of the resolution power due to size of the sample is remarkable.

Figure 7A:
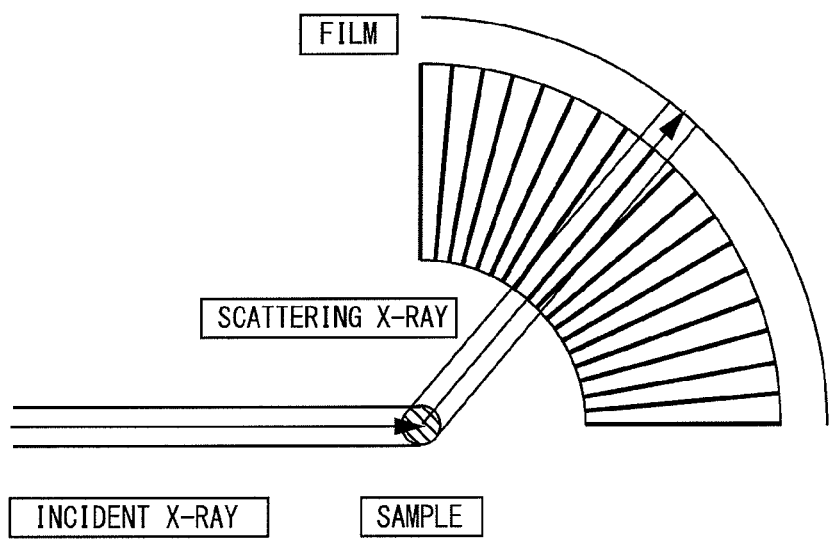
FIGS. 7A and 7B are views for explaining an eclipse (i.e., the shielding), within the analyzer made up with fan-shaped slits and parallel slits, in the conventional art.
Figure 7B:
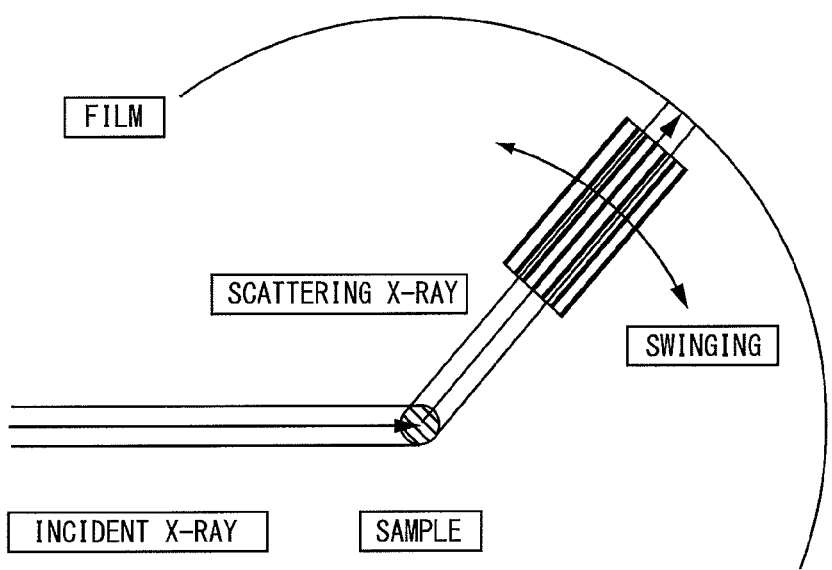

FIG. 7A shows the condition of the analyzer made from the fan-shaped slits, and as is apparent from the figure, a part of the scattering X-ray is shielded by a slit, which is partitioned in the fan-shaped by a metal foil. In particular, when conducting identification or structural analysis upon a powdered crystal, the scattering diffracted X-ray obtained comes to be thick, depending on size of the sample, for example, and this lowers a detection efficiency; i.e., generating remarkable reduction of measuring strength or intensity. Also, FIG. 7B shows the condition of the analyzer made from the parallel slits, but herein also is generated the reduction of resolution power, in particular, when the scattering diffracted X-ray is thick.

Figure 8A:
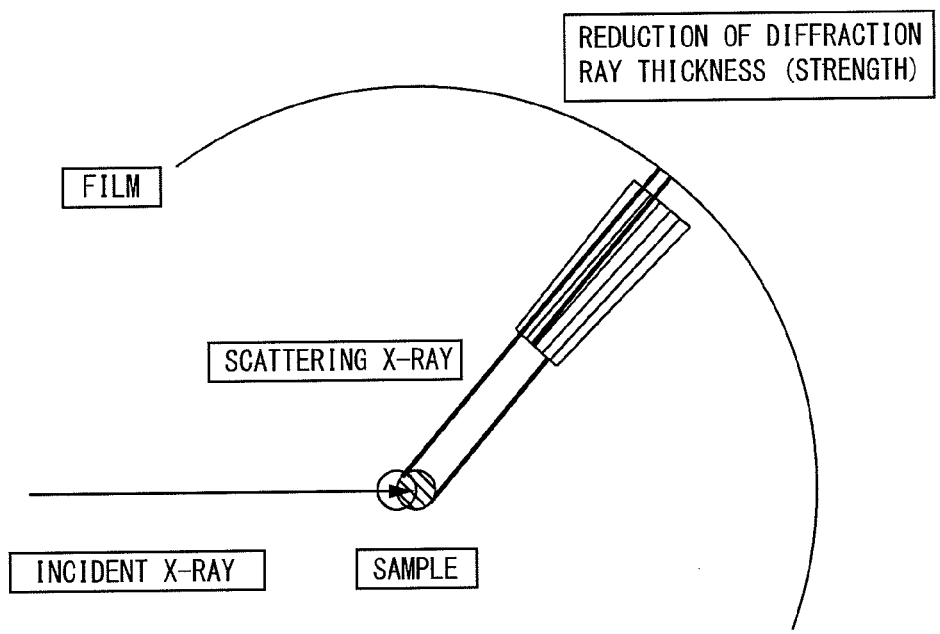
FIGS. 8A and 8B are views for explaining an angular error due to the position where the sample is amounted, within the analyzer made up with fan-shaped slits and parallel slits, in the conventional art.
Figure 8B:
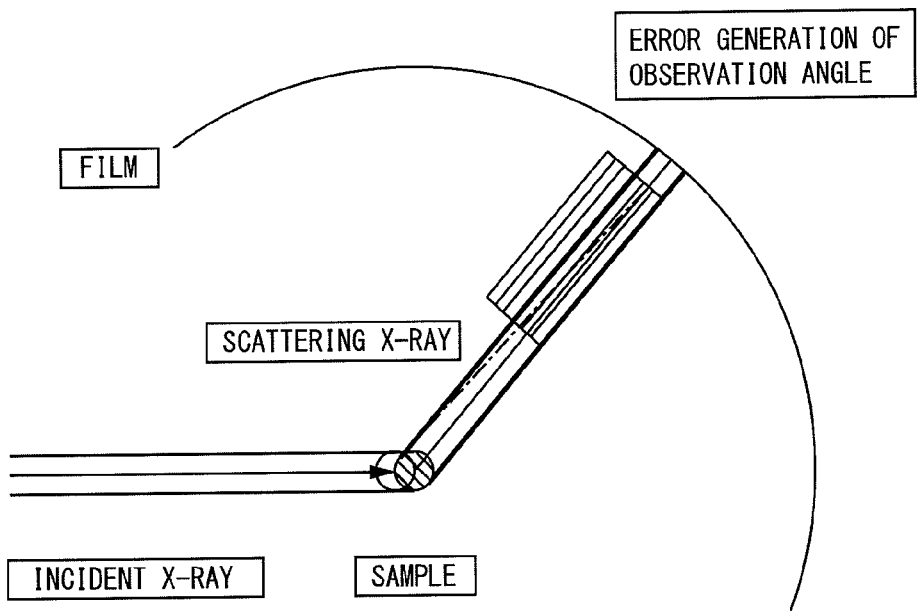

Further, FIG. 8A shows the condition of the analyzer made from the fan-shaped slits, in particular, when the position shift occurs, i.e., where the sample is mounted, herein also, as is apparent from the figure, a part of the scattering X-ray is shielded by the slit of the metal foil, and this lowers the detection efficiency and reduces the measuring strength or intensity. In addition thereto, FIG. 8B shows the condition of the analyzer made from the parallel slits, in particular, when the position shift occurs, i.e., where the sample is mounted, herein a shift is generated in an observing angle.

Figure 2:
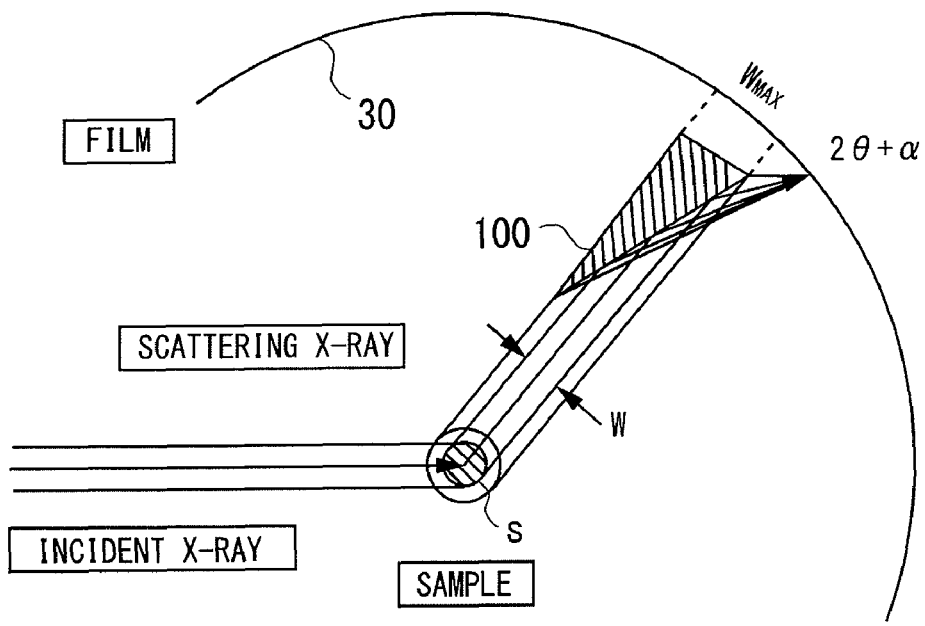
FIG. 2 is a view for explaining the principle of an analyzer utilizing a mirror made from artificial multi-layers, within the X-ray diffraction measuring apparatus of the present invention.

Then, according to the present invention, as is shown in FIG. 2 attached herewith, in the place of the analyzer, which is made from the fan-shaped slits or the parallel slits, of the metal foil, according to the conventional arts mentioned above, there is applied a mirror 100 made from an artificial multi-layer films having a parabolic surface. However, this mirror 100 is, as is disclosed in Japanese Patent No. 3721305, for example, a multi- or an inclined multi-layer Bragg X-ray reflection surface on the parabolic surface, thereby functioning to focus an incident X-ray (i.e., the scattering X-ray due to the diffraction in the sample), and it reflects the X-ray only when it satisfies the following Bragg's equation:

$$n\lambda = 2d \sin(\theta) \tag{Eq. 1}$$

where, n=a degree of reflection, λ=wavelength of incident radiation (i.e., X-ray), d=a layer preset spacing or lattice spacing of the Bragg's structure, and θ=an incident angle.

Also, since this mirror 100 made from the artificial multi-layers is able to resolve energy of the incident X-ray, it is possible to delete (or cut) a noise component, i.e., an excessive scattering X-ray, other than the X-ray diffracted from the sample, to be detected inherently, such as, the above-mentioned stray radiations, inelastic scattering, fluorescence, etc., for example, as well as, to increase an angular accuracy thereof.

Thus, with the analyzer using the mirror 100 mentioned above, i.e., being made from the artificial multi-layers and having the parabolic surface, according to the present invention, as is apparent from FIG. 2, the scattering X-ray obtained through the diffraction in the sample S is focused on the Bragg's X-ray reflector surface upon the parabolic surface of the mirror 100 mentioned above, which is disposed surrounding around the sample S, and it reaches onto the X-ray film 30, which builds up the X-ray detecting means, so as to expose that X-ray film, and thereby detecting the strength or intensity thereof. However, in this instance, it is preferable for the Bragg's X-ray reflector surface upon the parabolic surface of the mirror 100 mentioned above, to be formed to cover a region corresponding to a predetermined resolution power required (i.e., a half width "w" of diffracted ray), by taking the width ($W_{max}$) of the scattering X-ray obtained from the sample S into the consideration thereof. As a result thereof, as is apparent from the figure, the scattering X-ray having a predetermined region (or width) can reach to the position, which is shifted by a predetermined angle into the reflecting direction on the X-ray film (i.e., 2θ+α in FIG. 1B).

Figure 3:
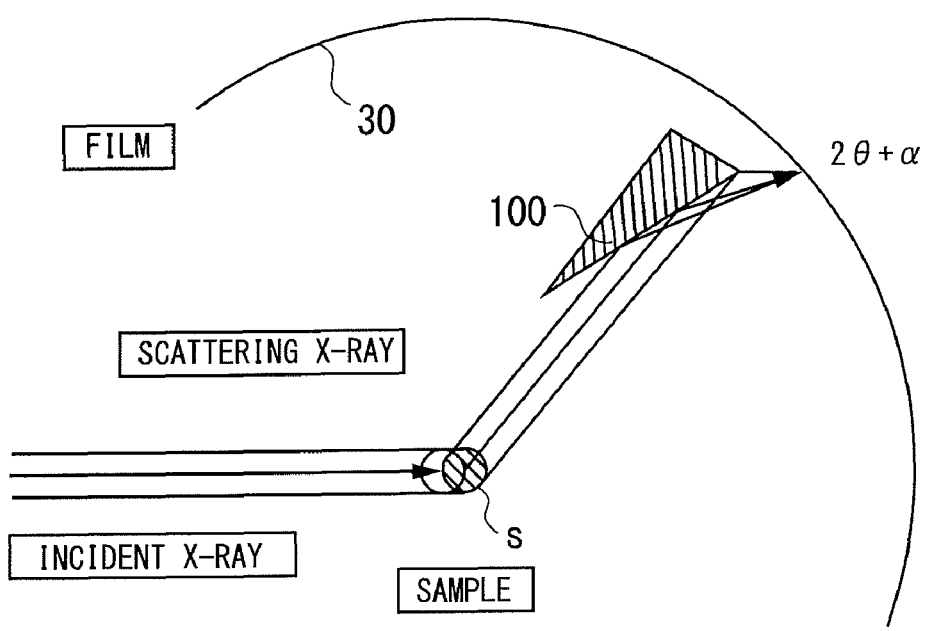
FIG. 3 is a view for explaining dissolution of ill influences due to an error of position where a sample is mounted, within the analyzer utilizing the mirror made from artificial multi-layers mentioned above.

In addition thereto, with the analyzer using the mirror 100 mentioned above, i.e., being made from the artificial multi-layers and having the parabolic surface, according to the present invention, as is apparent from FIG. 3, it is possible to detect the scattering X-ray obtained from the sample S while focusing it at a predetermined position on the X-ray film (i.e., 2θ+α), even in case where the position where the sample S moves from where it should be mounted (i.e., shifted).

As was mentioned above, with the analyzer using the mirror 100 mentioned above, i.e., being made from the artificial multi-layers and having the parabolic surface therein, according to the present invention, it is possible to dissolve the lowering in measuring strength or intensity with dissolving the reduction of the scattering ray (i.e., the diffracted X-ray) due to the eclipse (or shielding) by the analyzer, and further it is also possible to achieve the X-ray diffraction measuring apparatus equipped with the Debye-Scherrer optical system therein, without the lowering of resolution power depending on the size of the sample.

Following to the above, explanation will be made on the more detailed structures of the X-ray diffraction measuring apparatus according to the present invention, the principle of which was explained in the above, by referring to FIGS. 4 and 5 attached herewith.

Figure 4:
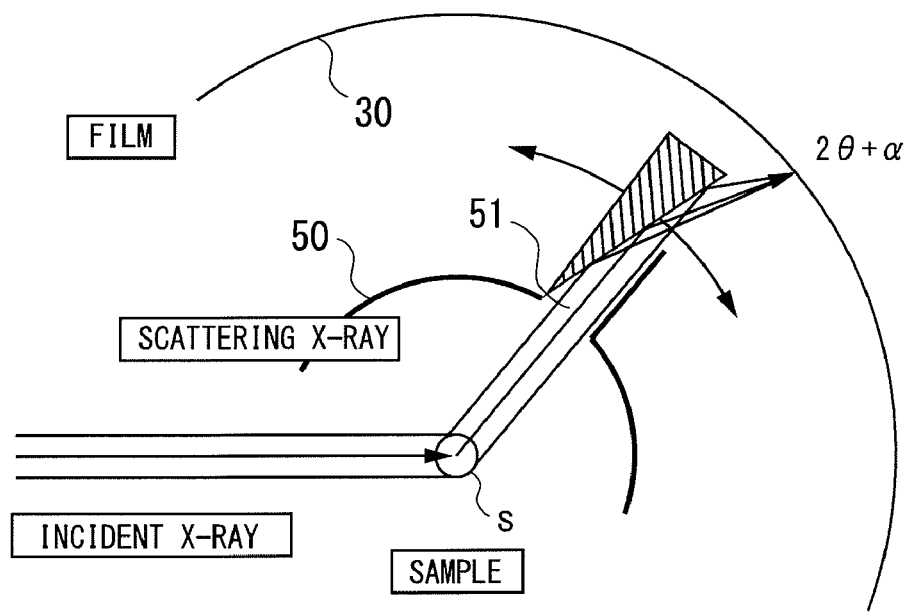
FIG. 4 is a view for showing an example of the detailed structures of the X-ray diffraction measuring apparatus having the Debye-Scherrer optical system therein, according to the embodiment of the present invention.

First of all, FIG. 4 shows the analyzer using the mirror 100 made from the artificial multi-layers mentioned above therein, being able to swing (or rotate) around the sample S, as is shown by arrows in the figure, wherein the above-mentioned mirror 100 is attached on a cutout portion 51, which is formed in a part of a metal-made rotating member 50 (i.e., an X-ray protection wall) shaped in a semi-circle covering around that sample S. With this the X-ray diffraction measuring apparatus, the scattering X-ray obtained from the sample S is exposed (sensed) with focusing it at the predetermined position on the X-ray film (i.e., 2θ+α), while rotationally shifting the rotating member 50 (i.e., the X-ray protection wall) 50 by a predetermined angle through an electric-powered motor, etc., for example, but not shown in the figure, and thereby it is possible to obtain the Debye rings, preferably, including an error (or shifting) of the position where the sample is mounted, without the lowering in measuring strength or intensity and/or the lowering in resolution power thereof.

Figure 5:
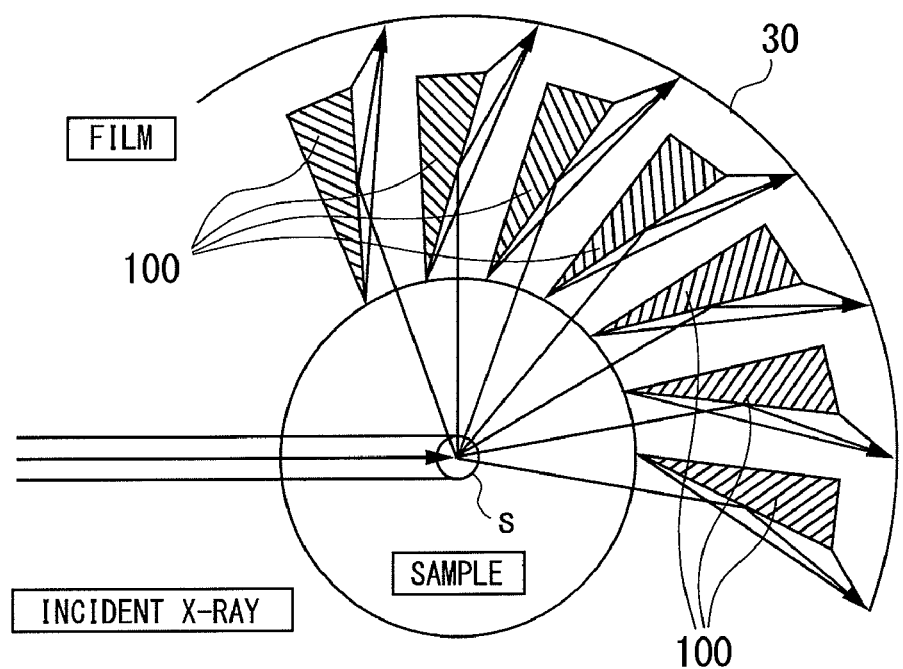
FIG. 5 is a view for showing other example of the detailed structures of the X-ray diffraction measuring apparatus having the Debye-Scherrer optical system therein, according to the embodiment of the present invention.

Further, FIG. 5 shows the structures of the X-ray diffraction measuring apparatus attached with the mirrors 100, each made from the artificial multi-layers mentioned above, in a plural number thereof, centering around the sample S. Thus, as is apparent from the figure, the plural numbers of the mirrors 100, each being made from the artificial multi-layers, are mounted thereon, surrounding around the sample S, and with this, it is possible to reduce or bring the swing region thereof to be small.

Also, with the embodiment mentioned above, although the explanation was given on the X-ray film 30, as an example, as a member for building up the X-ray detector means, however the present invention should not be restricted only to this, and other than that, it is also possible to build up the detector means by a two-dimensional detector shaped to be about cylindrical, such as, an imaging plate, a CCD two-dimensional detector, etc. Furthermore, because of using data in the vicinity of the equatorial surface of the X-ray diffraction Debye rings, it is also possible to utilize a one-dimensional detector in the place of the two-dimensional detector mentioned above.

Figure 6:
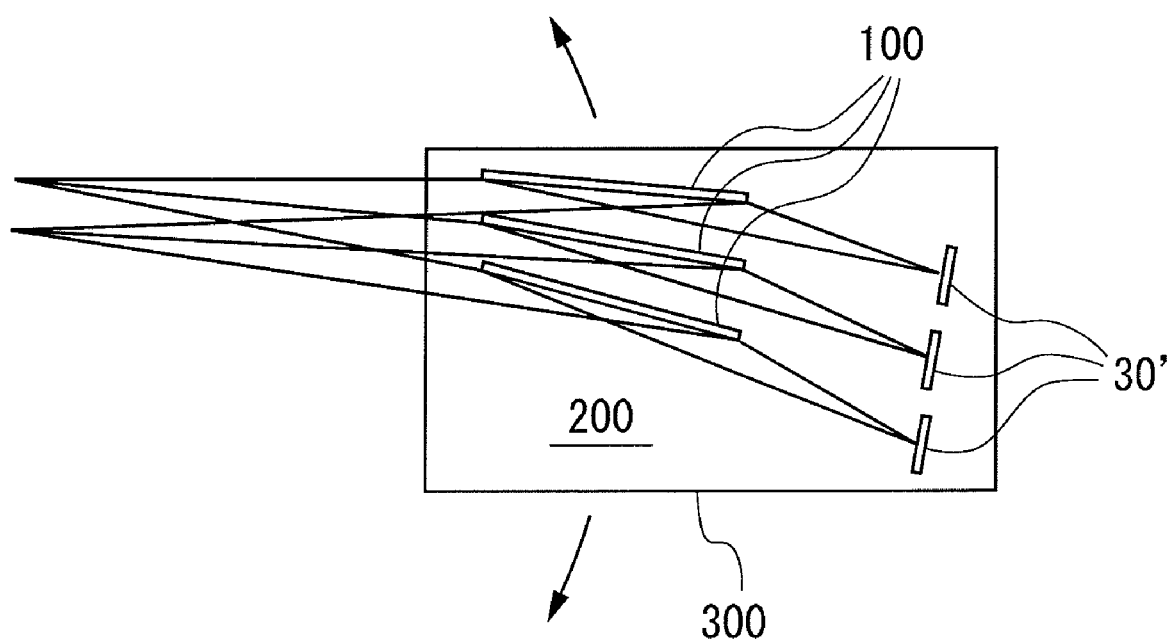
FIG. 6 is a view for showing the X-ray diffraction measuring apparatus having the Debye-Scherrer optical system therein, but according to other embodiment of the present invention.

Moreover, as other embodiment of the present invention, in the place of the analyzer made from the fan-shaped slit explained in the above (i.e., the fan-shaped slit, being formed with the mirror 100 of the artificial multi-layers thereon), for example, as is shown in FIG. 6 attached herewith, it is also possible to use an analyzer, in which the mirror 100 of the artificial multi-layers is made plate-like and this analyzer is mounted in a plural number thereof, in a fan-like manner (i.e., a multi-layer mirror 200 having multi mirrors), thereby to increase a detection efficiency thereof.

It is possible to apply the above into a high-speed measurement under a TDI mode with using the one-dimensional (or the two-dimensional) detector. Thus, in the example shown in this FIG. 6, (1) the multi-mirror 200 is made by combining the multi-layer mirrors 200 and a detector element 30' as a unit (see the reference numeral 300 in FIG. 6), (2) a CCD or a SSD is used as the detector 30', and (3) measurement is made while scanning in the rotation direction (see arrows in the figure) while keeping that combination shown in FIG. 6. Further, with the example shown in this FIG. 6, it is possible to obtain the detection efficiency, approximately as 3-times large, through the high-speed measurement mentioned above, and that detection efficiency can be increased, further, depending on a number of combinations of the mirrors and the crystals.

Next, hereinafter will be given the explanation about the details of the high-speed measurement mentioned above. Two (2) sets of detectors are mounted with shifting in front and back by $\Delta\theta$, respectively, with respect to the position of a central detector (including the mirror) (i.e., 2θ). In case when conducting the measurement at a center angle $2\theta_0$, data of the detectors are $2\theta_0$, $2\theta_0+\Delta\theta$ and $2\theta_0-\Delta\theta$, respectively, and they are accumulated (or added) as the strength or intensity data at the respective positions. Thereafter, after moving or changing the angle 2θ, by an arbitrary step, the measurement is conducted. As a result thereof, if the step for the measurement is a division by an integer of width between the detectors (i.e., $\Delta\theta$), it means that the measurement is made by three (3) times, at one angle each. Thus, it means that the measurement can be done at an efficiency of three (3) times by only one (1) time of scanning.

While we have shown and described several embodiments in accordance with our invention, it should be understood that disclosed embodiments are susceptible of changes and modifications without departing from the scope of the invention. Therefore, we do not intend to be bound by the details shown and described herein but intend to cover all such changes and modifications that fall within the ambit of the appended claims.

What is claimed is:

1. An X-ray diffraction measuring apparatus equipped with Debye-Scherrer optical system therein, comprising:
   a means for generating a characteristic X-ray to be irradiated upon a sample to be measured;
   an X-ray detector means being disposed to surround said sample around; and
   a focusing means, being disposed between said sample and said X-ray detector means, for collecting an X-ray scattering from said sample covering over a predetermined angle, in a peripheral direction, around said sample, and for focusing and irradiating it upon said X-ray detector means.

2. The X-ray diffraction measuring apparatus equipped with Debye-Scherrer optical system therein, as described in the claim 1, wherein said focusing means are attached in a plural number thereof, on a front surface of said X-ray detector means.

3. The X-ray diffraction measuring apparatus equipped with Debye-Scherrer optical system therein, as described in the claim 2, wherein said focusing means is built up with a mirror, which is made of artificial multi-layers having a parabolic surface.

4. The X-ray diffraction measuring apparatus equipped with Debye-Scherrer optical system therein, as described in the claim 2, wherein said X-ray detector means is built up with a one-dimensional detector.

5. The X-ray diffraction measuring apparatus equipped with Debye-Scherrer optical system therein, as described in the claim 1, wherein said focusing means is attached to be movable, on a front surface of said X-ray detector means.

6. The X-ray diffraction measuring apparatus equipped with Debye-Scherrer optical system therein, as described in the claim 5, wherein said focusing means is built up with a mirror, which is made of artificial multi-layers having a parabolic surface.

7. The X-ray diffraction measuring apparatus equipped with Debye-Scherrer optical system therein, as described in the claim 5, wherein said X-ray detector means is built up with a one-dimensional detector.

8. The X-ray diffraction measuring apparatus equipped with Debye-Scherrer optical system therein, as described in the claim 1, wherein said focusing means is built up with a mirror, which is made of artificial multi-layers having a parabolic surface.

9. The X-ray diffraction measuring apparatus equipped with Debye-Scherrer optical system therein, as described in the claim 1, wherein said X-ray detector means is built up with either one of a one-dimensional detector and a two-dimensional detector.

10. The X-ray diffraction measuring apparatus equipped with Debye-Scherrer optical system therein, as described in the claim 9, wherein the two-dimensional detector for building up said X-ray detector means is made from at least one of an X-ray sensitive film, an imaging plate, a CCD two-dimensional detector, a PSD one-dimensional detector.

11. The X-ray diffraction measuring apparatus equipped with Debye-Scherrer optical system therein, as described in the claim 1, wherein said X-ray detector means is built up with a one-dimensional detector.

12. The X-ray diffraction measuring apparatus, as described in claim 1, wherein the X-ray detector means is disposed proximate to a focusing position of said focusing means.

13. An X-ray diffraction measuring method for Debye-Scherrer optical system, comprising the following steps of:
    irradiating a characteristic X-ray generated to a sample;
    collecting and focusing a scattering X-ray obtained through irradiation of said X-ray to said sample, covering over a predetermined angle around said sample; and
    obtaining a Debye ring by focusing and irradiating the scattering X-ray at a predetermined position on an X-ray detector means, being disposed in a peripheral direction, surrounding around said sample.

14. The X-ray diffraction measuring method for Debye-Scherrer optical system, as claimed in the claim 13, wherein the scattering X-ray is collected and focused by a mirror made of artificial multi-layers, covering over a predetermined angle around said sample, and is focused and irradiated at a predetermined position on the X-ray detector means, which is disposed to surround said sample around.

* * * * *